(12) United States Patent
Skuratowicz

(10) Patent No.: US 7,101,996 B2
(45) Date of Patent: Sep. 5, 2006

(54) PROCESS FOR PREPARING PURIFIED FRACTIONS OF HEMICELLULOSE AND CELLULOSE-HEMICELLULOSE COMPLEXES FROM ALKALI TREATED FIBER AND PRODUCTS MADE BY THE PROCESS

(75) Inventor: Roman Skuratowicz, Hickory Hills, IL (US)

(73) Assignee: Corn Products International, Inc., Westchester, IL (US)

( * ) Notice: Subject to any disclaimer, the term of this patent is extended or adjusted under 35 U.S.C. 154(b) by 225 days.

(21) Appl. No.: 10/668,951

(22) Filed: Sep. 23, 2003

(65) Prior Publication Data

US 2005/0061457 A1    Mar. 24, 2005

(51) Int. Cl.
*C08B 1/00* (2006.01)
*C07H 1/00* (2006.01)
*C07H 1/06* (2006.01)
*C07H 1/08* (2006.01)

(52) U.S. Cl. .................. 536/56; 536/124; 536/127; 536/128

(58) Field of Classification Search .................. 536/56, 536/124, 127, 128
See application file for complete search history.

(56) References Cited

U.S. PATENT DOCUMENTS

| 2,868,778 A | 1/1959 | Watson et al. ............... 260/209 |
| 3,716,526 A | 2/1973 | Schweiger .................. 260/212 |
| 3,935,022 A | 1/1976 | Sihtola ........................ 106/163 |
| 4,038,481 A | 7/1977 | Antrim et al. ................. 536/56 |
| 4,097,666 A | 6/1978 | Johnson et al. ................ 536/57 |
| 4,104,463 A | 8/1978 | Antrim et al. ................. 536/56 |
| 5,530,112 A | 6/1996 | Greenshields et al. ... 536/123.1 |
| 6,033,712 A | 3/2000 | Greenshields et al. ...... 426/573 |
| 6,174,549 B1 | 1/2001 | Greenshields et al. ...... 424/488 |
| 2001/0020091 A1 | 9/2001 | Buchanan et al. .......... 536/123 |

*Primary Examiner*—Shaojia Anna Jiang
*Assistant Examiner*—Everertt White
(74) *Attorney, Agent, or Firm*—Norris, McLaughlin & Marcus

(57) ABSTRACT

A process for obtaining purified hemicellulose, cellulose and cellulose-hemicellulose complexes comprising the steps of adding alcohol to caustic liquor from alkali extraction of fiber to precipitate the hemicellulose and the simultaneous, or about simultaneous, density separation of hemicellulose from the caustic liquor. The alcohol transforms the soluble high molecular weight hemicellulose into a light precipitate which floats on top of the caustic liquor solution. The caustic liquor can be subjected to a second separation step whereby the insoluble components (e.g. cellulose and cellulose-hemicellulose complexes) can be removed from the caustic liquor.

12 Claims, No Drawings

PROCESS FOR PREPARING PURIFIED FRACTIONS OF HEMICELLULOSE AND CELLULOSE-HEMICELLULOSE COMPLEXES FROM ALKALI TREATED FIBER AND PRODUCTS MADE BY THE PROCESS

BACKGROUND OF THE INVENTION

1. Field of the Invention

The invention pertains to a process for preparing purified fractions of hemicellulose and cellulose-hemicellulose complexes from alkali treated fiber. Specifically, the process involves the dispersion of alcohol in caustic liquor from alkali treatment of fiber to separate hemicellulose from impurities. The hemicellulose physically separates from the impurities, including cellulose and cellulose-hemicellulose complexes, by floating to the top of the caustic liquor after precipitation with alcohol. Density separation techniques are used to separate the floating precipitated hemicellulose simultaneously, or about simultaneously, with the formation of floating hemicellulose precipitate. The insoluble cellulose and cellulose-hemicellulose complexes can be removed from the caustic liquor by a further separation step.

2. The Prior Art

Fiber consists of hemicellulose, cellulose, some small amount of lignin, oil, starch, and protein. Alkali treatment of fiber, such as corn fiber or other seed fibers, solubilizes about two thirds of the available hemicellulose, and makes an insoluble cellulose-hemicellulose material. Both materials have value as hydrocolloids, however, a complex and difficult separation and refinement has been traditionally necessary to separate the material to produce separate products.

Also, the hemicellulose fraction will have impurities from the alkali separation. Purified hemicellulose has many commercial uses, including uses in the processed food industry; however the value of hemicellulose as a commercial product becomes limited if impurities obtained during the extraction of hemicellulose from fiber remain present in the final hemicellulose product.

U.S. Pat. No. 3,716,526 describes a process for obtaining refined hemicellulose comprising the steps of suspending powdered dried crude hemicellulose in aqueous organic acid and/or organic solvent and then physically separating impurities in the suspension to obtain purified hemicellulose. U.S. Pat. No. 2,868,778 describes a process involving precipitation of hemicellulose from extract by use of a solvent. U.S. Pat. No. 3,935,022 describes a method for treating caustic liquor, such as that originating in the alkaline refining of pulp or viscose manufacture, with one or more organic compounds which have a boiling point below 100° C. and are miscible with water (preferably ethanol) and sodium hydroxide to precipitate hemicellulose from the caustic liquor and then separating the precipitate by ordinary techniques of separation such as filtration, sedimentation and decantation, centrifugation and the like.

We have discovered a process whereby hemicellulose can be separated from caustic liquor by the simultaneous, or about simultaneous, precipitation of the hemicellulose from alkali solutions containing hemicellulose as well as insoluble cellulose and cellulose-hemicellulose complexes, such that hemicellulose precipitate floats on the caustic liquor. Density separation techniques can be used to separate the floating precipitated hemicellulose from the caustic liquor. In the process, the hemicellulose precipitate floats on the top of the caustic liquor as a result of the nature of the alcohol solution used for precipitation and separation parameters. The precipitated hemicellulose is removed from the caustic liquor before it swells and settles into the fluid, mixing with the insoluble cellulose and cellulose-hemicellulose complexes. The cellulose and cellulose-hemicellulose complexes can then be separated from the caustic liquor in a subsequent separation step.

All parts and percentages in this Specification are on a weight-by-weight basis, unless stated otherwise.

SUMMARY OF THE INVENTION

The invention pertains to a process for the separation and removal of hemicellulose and insoluble cellulose and cellulose-hemicellulose complexes to produce two fractions of hydrocolloids. The separation occurs in the caustic liquor from solubilizing fiber with alkali. The process comprises the steps of alcohol precipitation of the hemicellulose from the caustic liquor, which transforms the soluble high molecular weight hemicellulose into a light precipitate that floats on top of the caustic liquor with the simultaneous, or about simultaneous, density separation of the hemicellulose precipitate from the caustic liquor before the hemicellulose absorbs sufficient water to cause it to swell and settle into the caustic liquor. The insoluble cellulose and cellulose-hemicellulose complexes can then be removed from the caustic liquor by a second separation step.

DETAILED DESCRIPTION OF THE INVENTION

The process comprises the steps of providing caustic liquor from the alkali extraction of hemicellulose, adding alcohol or a solution of alcohol in water to the caustic liquor to precipitate the hemicellulose and density separation of floating precipitated hemicellulose from the caustic liquor. The insoluble cellulose and cellulose-hemicellulose complexes can be removed from the caustic liquor in a second separation step. The step of adding alcohol to the caustic liquor to precipitate the hemicellulose is performed simultaneously, or about simultaneously, with the density separation of the hemicellulose from the caustic liquor, such that the separation occurs on an ongoing basis while hemicellulose precipitate forms and floats to the top of the caustic liquor. The density separation occurs prior to the hemicellulose absorbing water and swelling which will cause the hemicellulose to settle into the caustic liquor where it becomes more difficult to separate in its purified form from the insoluble components.

The hemicellulose is removed directly from the caustic liquor by density separation without any intermediate steps and prior to any, or any substantial amount, of the hemicellulose settling into the caustic liquor. Because none, or almost none of the hemicellulose, settles into the caustic liquor, the cellulose and cellulose-hemicellulose complexes are not contaminated, at least to a significant extent, by hemicellulose during the second separation step. Also, any impurities remain with the caustic liquor and are not separated with the precipitated hemicellulose, nor are they separated in the second separation step. Thus, the process can be used to obtain two separate purified hydrocolloid materials, both of which have value as commercial products.

Alkali extraction of hemicellulose from fiber is known in the art, and any technique known in the art may be used to provide the caustic liquor. The caustic liquor may be obtained by solubilizing hemicellulose from fiber under semi-dry conditions, such as the process described in the inventor's co-pending patent application LOW MOISTURE PROCESS FOR EXTRACTING HEMICELLULOSE, Ser. No. 10/350,610, filed Jan. 24, 2003, which is incorporated by reference herein in its entirety. The semi-dry process comprises agitating at least fiber, caustic and, optionally, added water at a moisture content from about 10% to about 60%, preferably from about 15% to about 50% and most preferably from about 20% to about 40% at speeds of about 300 rpm to about 2,000 rpm, preferably from about 500 rpm to 1,750 rpm. The amount of caustic may be about 10% to about 40%, preferably from about 10% to about 25%, by dry weight of the fiber.

Fiber sources include spent flake fiber, corn hull fiber, or other vegetable or seed fibers, preferably rich in hemicellulose. The process is particularly suitable for corn fibers, which include crude fiber, typically described as feed, and more finished products such as dietary corn fiber which is made for human consumption. Crude fiber or feed generally contains from about 20% to about 40% hemicellulose and dietary corn fiber generally contains from about 50% to about 80% hemicellulose. Any strong base can be used for the alkali to extract the cellulose, hemicellulose and cellulose-hemicellulose complexes from the fiber. Preferably, however, alkali metal hydroxides, such as sodium hydroxide and potassium hydroxide, are used. Combinations of alkalis may also be used.

Alcohols useful for obtaining the floating precipitated hemicellulose include those selected from the group consisting of methanol, ethanol, isopropanol, tertiary butyl alcohol, acetone and the like, and combinations thereof. We have found that the best results are achieved with methanol in solution with water. Alcohol in a solution having an alcohol to water ratio of about 1:1 to about 20:1, most preferably about 3:1 to about 9:1, is generally necessary to obtain the floating precipitate. The alcohol solution is obtained by either adding sufficient alcohol so that the alcohol is in solution with water in the caustic liquor at the appropriate alcohol to water ratio or an alcohol and water solution can be added to the caustic liquor.

Alcohol precipitation of the hemicellulose will transform the soluble high molecular weight hemicellulose into a light precipitate. As the hemicellulose precipitates it floats on top of the caustic liquor solution. Flocculation aids are not needed for this precipitate to float on top of the caustic liquor. Separators and cyclones, such as starch/gluten cyclones, available from Westfalia Separator, Inc., Northvale, N.J., USA can be used to separate the floating hemicellulose precipitate from the caustic liquor. The separated hemicellulose is removed from the top of the caustic liquor and can then be dried. The remaining caustic liquor is removed from the density separation device and can be subjected to a second separation step to separate the insoluble portions, primarily cellulose and cellulose-hemicellulose complexes, from the caustic liquor. The second separation step may be performed in a separator or cyclone similar to those discussed above or with other separation technology, such as filtration and the like.

Optionally, peroxide can be added during the extraction step or as a separate step to improve hemicellulose color. Hydrogen peroxide is preferred; however sodium hypocholorite or similar oxidizing components can be used. Up to about 100% peroxide, preferably from about 20% to about 40%, by weight based on the amount of fiber, can be used.

EXAMPLES

Example 1

Sixty grams of spray dried hemicellulose was dispersed in 600 milliliters of water, and then an additional 400 milliliters of water was added. Next, 3 liters of methanol was added to the dispersed hemicellulose. The majority of the pure hemicellulose floated.

Example 2

Alkali treated corn fiber is produced by reacting 90 grams (dry basis) corn hull fiber with 16.4 grams sodium hydroxide in a semi dry reaction at 45% solids for one hour at 100° F., followed by oven drying at 100° F. for 12 hours. The resulting material was dispersed in 250 milliliters water and treated with 750 milliliters methanol. The soluble hemicellulose portion precipitated and floated. The hemicellulose precipitate was immediately separated by laboratory decantation techniques.

Example 3

Twenty grams of spray dried hemicellulose was dispersed in 200 milliliters of water, and then an additional 100 milliliters of water was added. Next, 1 liter of ethanol was added to the dispersed hemicellulose. The hemicellulose separated and initially floated, however, over time, almost all the material sank (sediment) as a result of the solvent saturating the hemicellulose particles.

What is claimed is:

1. A process for the separation of purified hemicellulose from insoluble cellulose and cellulose-hemicellulose complexes in caustic liquor from solubilizing fiber with alkali comprising the steps of adding alcohol to the caustic liquor to precipitate the hemicellulose so that the hemicellulose floats on top of the caustic liquor and alcohol and density separation of the floating hemicellulose precipitate from the insoluble cellulose and cellulose-hemicellulose complexes in caustic liquor simultaneously with the precipitation of the hemicellulose wherein the ratio of alcohol to water in the caustic liquor is about 3:1 to about 9:1.

2. The process of claim 1 wherein the fiber is solubilized with alkali at a moisture content from about 10% to about 60% with agitation at speeds of about 300 rpm to about 2,000 rpm.

3. The process of claim 1 wherein the alcohol is selected from the group consisting of methanol, ethanol, isopropanol, tertiary butyl alcohol, and combinations thereof.

4. The process of claim 1 wherein the density separation occurs in a cyclone or a decanter.

5. The process of claim 1 wherein the fiber is spent flake fiber or corn hull fiber.

6. The process of claim 5 wherein the corn hull fiber is selected from the group consisting of crude fiber, dietary fiber and combinations thereof.

7. The process of claim 1 wherein the alkali is an alkali metal hydroxide.

8. The process of claim 7 wherein the alkali metal hydroxide is selected from the group consisting of sodium hydroxide, potassium hydroxide and combinations thereof.

9. The process of claim 1 comprising the additional step of adding peroxide.

10. The process of claim 9 wherein the peroxide is added when the fiber is solubilized with alkali.

11. A process for separating purified hemicellulose from insoluble cellulose and cellulose-hemicellulose complex in caustic liquor from solubilizing fiber with alkali comprising the steps of a) adding an alcohol selected from the group consisting of ethanol and methanol to the caustic liquor wherein the ratio of alcohol to water is about 3:1 to about 9:1 to precipitate the hemicellulose so that the hemicellulose floats on top of the caustic liquor and alcohol, b) density separation of the floating hemicellulose precipitate in a density separation device simultaneously with the precipitation of the hemicellulose, and c) removal of the caustic liquor from the density separation device.

12. A process for separating purified hemicellulose from insoluble cellulose and cellulose-hemicellulose complexes in caustic liquor from solubilizing fiber with alkali comprising the steps of adding alcohol to the caustic liquor to cause the hemicellulose to float on top of the caustic liquor and alcohol and separating the floating hemicellulose before it absorbs sufficient water to cause it to swell and settle into the caustic liquor wherein the ratio of alcohol to water in the caustic liquor is about 3:1 to about 9:1.

* * * * *